United States Patent [19]

Bankmann et al.

[11] Patent Number: 5,387,726

[45] Date of Patent: Feb. 7, 1995

[54] SELECTIVE CATALYTIC HYDROGENATION OF AROMATIC ALDEHYDES

[75] Inventors: Martin Bankmann, Gelnhausen; Reinhold Brand, Hanau; Andreas Freund, Moemrbris; Thomas Tacke, Freigericht, all of Germany

[73] Assignee: Degussa Aktiengesellschaft, Frankfurt am Main, Germany

[21] Appl. No.: 179,621

[22] Filed: Jan. 7, 1994

[30] Foreign Application Priority Data

Jan. 8, 1993 [DE] Germany ................................ 4300297

[51] Int. Cl.⁶ ..................... C07C 29/141; C07C 27/04
[52] U.S. Cl. ................................. 568/814; 568/862
[58] Field of Search ................ 568/814, 626, 862

[56] References Cited

U.S. PATENT DOCUMENTS

| | | | |
|---|---|---|---|
| 4,721,808 | 1/1988 | Lillwitz et al. | 562/473 |
| 4,743,577 | 5/1988 | Schroeder et al. | 502/326 |
| 4,812,594 | 3/1989 | Petty-Weeks | 562/473 |

FOREIGN PATENT DOCUMENTS

| | | | |
|---|---|---|---|
| 0265137 | 4/1988 | European Pat. Off. | C07C 63/26 |
| 535565 | 4/1993 | European Pat. Off. | |
| 2709525 | 9/1977 | Germany | C07C 63/26 |
| 899009 | 6/1962 | United Kingdom | |
| 1144257 | 3/1969 | United Kingdom | C07C 31/34 |
| 1159967 | 7/1969 | United Kingdom | |

OTHER PUBLICATIONS

Zymalkowski, "Katalytische Hydrierungen", 1965, pp. 103–105.

Catalysis Today, Bankmann et al. (1992), "Forming of High Surface TiO2 to Catalyst Supports", pp. 225–242.
K. Weissermel et al., Ind. Org. Chemie, pp. 414–424.
J. Chem. Soc., Faraday Trans. 1, 1988, 84(5), An Infrared Spectroscopic Study of Anatase Properties, pp. 1617–1637.
Zeitschrift fur Physikalische Chemie Neue Folge, Bd. 162, J. A. R. van Veen, pp. 215–229.
U.S. Pat. No. T880,007 (Official Gazette, 1970, vol. 880, No. 4, p. 1162.

*Primary Examiner*—Werren B. Lone
*Attorney, Agent, or Firm*—Beveridge, DeGrandi, Weilacher & Young

[57] ABSTRACT

A process is disclosed for the selective catalytic hydrogenation of carbonyl groups in aromatic aldehydes of the formula:

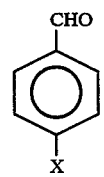

in which X is carboxyl, methyl or a halogen, to give the corresponding alcohols and methyl compounds. The catalytic hydrogenation is performed with the addition of a solvent optionally in the presence of organic acids on a shaped support catalyst containing a platinum group metal on a support made from titanium oxide in the presence of hydrogen at hydrogen partial pressures of 5 to 50 bar and temperatures of 100° to 300° C.

12 Claims, No Drawings

SELECTIVE CATALYTIC HYDROGENATION OF AROMATIC ALDEHYDES

INTRODUCTION AND BACKGROUND

The present invention relates to a process for the selective catalytic hydrogenation of carbonyl groups in aromatic aldehydes of the formula:

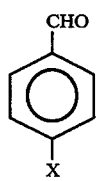

wherein X is a carboxyl, methyl or a halogen, to yield the corresponding alcohols and methyl compounds.

Selective catalytic hydrogenation of aromatic aldehydes to give benzyl alcohols or the toluene compound which is produced as a result of hydrogenation, is of great importance for the preparation of organic intermediates in the field of fine chemicals.

This enables a method of obtaining these classes of products which is technically simple to accomplish and which represents a powerful alternative synthetic pathway for the preparation of substituted benzyl alcohols, which are otherwise obtainable using organic preparative methods via the crossed Cannizarro reaction of an aromatic aldehyde with formaldehyde.

In "Katalytische Hydrierungen" by F. Zymalkowski (Ferdinand Enke Verlag, Stuttgart, 1965; pages 103-105), palladium on activated carbon (Pd/C) and nickel catalysts are mentioned as suitable hydrogenation catalysts. Copper chromite catalysts for the selective hydrogenation of 4-chlorobenzaldehyde to give 4-chloro-1-hydroxymethyl-benzene are known from GB 1,144,257. Noble metal/titanium dioxide catalysts (NM/TiO$_2$) for the hydrogenation of aromatic aldehydes are described in "Forming of High Surface Area TiO$_2$ to Catalysts Supports" by Bankmann et al. in Catalysis Today 14 (1992) 225-242.

The selective hydrogenation of aromatic aldehydes has attained outstanding significance in the area of purifying terephthalic acid and also p-hydroxymethylbenzoic acid.

Terephthalic acid is prepared by radical catalyzed liquid phase oxidation of p-xylene in acetic acid using Co/Mn/acetate catalysts and bromine activation (K. Weissermel, H. J. Arpe in "Industrieller Organische Chemie"; Verlag Chemie, Weinheim 1988, pages 415-424). Terephthalic acid prepared in this way contains 4-carboxybenzaldehyde as an impurity, and this interferes with the subsequent polymerisation process intended to give polyesters. Therefore in the purification stage of the process, the crude terephthalic acid is dissolved under pressure in water at 275° to 300° C. and, in the presence of Pd/C or Rh/C catalysts, hydrogenated to give p-hydroxymethylbenzoic acid and p-methylbenzoic acid, or decarbonylated to give benzoic acid.

The reaction products mentioned above can be removed from the crude terephthalic acid by fractional crystallisation due to their greater solubility in water as compared with 4-carboxybenzaldehyde and in particular terephthalic acid.

Terephthalic acid is obtained in a so-called fiber-pure grade with a purity of 99.99%, which is then reacted, in the form of dimethylterephthalate, with diol components (preferably ethylene glycol) to give polyethyleneterephthalate (PET). The main use for this polyester is in the fiber industry.

According to EP 0 265 137, 0.5% Pd/C (coconut carbon) catalysts are preferably used for hydrogenating 4-carboxybenzaldehyde during purification procedures which conform to the relevant TA Standard.

Other catalysts which are known for purification procedures which conform to the relevant TA Standard are bimetallic Pt-Rh/C or Pd-group VIII metal/C mixed catalysts from DE 27 09 525, Ni/kieselguhr catalysts from U.S. Defensive Publication No. 880 007 (Official Gazette 1970, Vol. 880, No. 4, page 1162) and Pd, Pt, Rh, Ni, Ru, Co or mixtures thereof on metal supports from the group Ti, Zr, W, Cr, Ni or alloys of these metals from U.S. Pat. No. 4,743,577.

One problem when using the NM/C (NM=noble metal) catalysts described is the mechanical abrasion of black carbon fixed-bed catalysts which produces "black dots" and means the purified terephthalic acid does not comply with the specifications for fiber quality.

Another technically relevant example of an industrial application of the selective hydrogenation of aromatic aldehydes is the catalytic purification of p-hydroxymethylbenzoic acid, an important monomer for the preparation of poly-paramethylenebenzoate.

p-hydroxymethylbenzoic acid is prepared by the electro-chemical reduction of terephthalic acid and contains traces of carboxybenzaldehyde. Purification requires highly selective hydrogenation of 4-carboxybenzaldehyde to give p-hydroxymethylbenzoic acid.

Hydrogenolysis to give p-methylbenzoic acid must not take place since this terminates chain-formation during the subsequent polymerisation process, as does 4-carboxybenzaldehyde.

Ni/kieselguhr is used at 50° C. according to U.S. Pat. No. 4,812,594 or Pt/C at 75° C. in an aqueous, basic solvent at a pH between 7 and 8 according to U.S. Pat. No. 4,721,808.

The disadvantage of the processes described in the patents is that high p-hydroxymethylbenzoic acid selectivity is only achieved at low temperatures. However, the solubility in water of the participating reaction partners is too low at these temperatures, so a basic solvent has to be used. This in turn has the disadvantage that additional basic and acidic additives complicate the process and make it more expensive to operate.

A further industrial application for the selective hydrogenation of aromatic aldehydes is known from JP 53 002 441. This involves the hydrogenation of p-toluylaldehyde to give p-hydroxymethyltoluene in the presence of p-xylene-methylether and methyl p-methylbenzoate on a PtO$_2$ catalyst doped with Fe.

An object of the present invention is to provide a process for the selective catalytic hydrogenation of aromatic aldehydes which avoids the disadvantages mentioned for the known processes.

Another object of the invention is to enable improved purification of crude terephthalic acid and p-hydroxymethylbenzoic acid and to permit the preparation of a whole class of fine chemicals. Another object of the invention is the provision of a method for preparing benzyl ether.

SUMMARY OF THE INVENTION

The first object is achieved by a process for the selective catalytic hydrogenation of the carbonyl group in aromatic aldehydes of the formula:

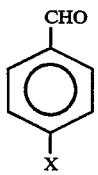

wherein X is carboxyl, methyl or a halogen, to yield the corresponding alcohols and methyl compounds. A feature of the process of the invention resides in that the aromatic aldehydes are hydrogenated with the addition of a solvent, optionally in the presence of organic acids, on a shaped support catalyst containing a platinum group metal on a support of titanium oxide in the presence of hydrogen at hydrogen partial pressures of 5 to 50 bar and temperatures of 100° to 300° C.

The process according to the invention is distinguished by high flexibility. By selecting the phase of the titanium oxide and thus the associated acidity of the titanium oxide support (anatase, rutile or physical mixtures or mixed phases of anatase and rutile in any ratios), the type of noble metal (platinum, palladium or rhodium), the profile of the noble metal (homogeneous distribution throughout or shell-shaped) and the noble metal content, tailor-made product distributions can be obtained over a wide range between hydrogenation to give benzyl alcohol, hydrogenolysis to give a toluene compound or decarboxylation to give benzoic acid. The term "shell-shaped" or "shell" catalyst is well understood in the art and is used in the same way herein.

DETAILED DESCRIPTION OF INVENTION

It was found that both precipitated titanium oxide and pyrogenic titanium oxide, prepared by flame hydrolysis from titanium tetrachloride, may be used for preparing the titanium oxide support.

Precipitated titanium oxide is usually present in the pure anatase modification form, while pyrogenic titanium oxide consists of a mixed phase of 75% anatase and 25% rutile, which can optionally be converted completely to the rutile phase by appropriate calcination of the shaped support made therefrom. The acidity of the titanium oxide is greatly reduced by this phase change. In the case of precipitated titanium oxides which are prepared by the sulfate process, the presence of sulfate leads to high acidity (C. Morterra, J. Chem. Soc. Faraday Trans. 1, 84 (1988), 1617–1637). The acidity of titanium oxide powders is determined by measuring the pH of a 4% strength aqueous suspension according to ASTM D 3830-80. Precipitated titanium oxide has a pH of less than 5, usually less than 3, depending on the residual sulfate content, while pyrogenic titanium oxide consisting of 75% anatase and 25% rutile has a pH between 3 and 5 and calcined pyrogenic titanium oxide consisting of 100% rutile has a pH between 5 and 7.

Titanium oxide grades with specific BET surface areas between 1 and 200 $m^2/g$, which are determined in accordance with DIN 66132 using nitrogen, are advantageous.

The supports are preferably prepared by extrusion. Here, precipitated titanium oxide powder or pyrogenic titanium oxide powder is moistened to a moisture content of 28 to 38% by adding 0.5 to 3% by weight of methyl cellulose, 0.2 to 3% by weight of lactic acid and water and kneading intensively at room temperature in a kneading unit. The resulting plastic (moldable) kneaded material is then extruded to give cylindrical supports with diameters of 1 to 5 mm and lengths of 5 to 10 mm.

The freshly prepared material is carefully dried at 70° C. for a period of 24 hours and then calcined to remove the organic additives. By selecting a calcination temperature in the range from 400° to 1000° C. and a period of calcination between 1 and 5 hours, the anatase/rutile ratio in the extruded supports can be specifically adjusted.

To obtain the original phase structure and specific surface areas of the starting material, calcination is preferably performed at 400° C. for only 1 hour.

By increasing the temperature to 700° C. and calcining for 5 hours, the phase structure of pyrogenic titanium oxide can be completely converted into rutile. The specific surface area is then reduced to about 10 $m^2/g$.

The supports prepared in this way have a total pore volume between 0.15 and 0.5 ml/g, which is composed of mesopores with diameters between 2 and 30 nm and macropores with diameters larger than 30 nm. There are no micropores with diameters less than 2 nm.

The total pore volume is determined arithmetically from the sum of the micro-, meso- and macropores. The micro- and mesopores are determined by plotting an $N_2$ isotherm and evaluating this according to BET, de Boer and Barret, Joyner, Halenda. Macropores are determined using the mercury injection method.

The supports have outstanding mechanical properties. The breaking or rupture strength, determined using a breaking strength tester from Erweka, Type TBH 28, is between 40 and 80N depending on the temperature and duration of calcination. These breaking strengths ensure that abrasion of the support is low and impurities in the reaction products caused therefrom are negligible.

These mechanical properties of the supports are produced without the addition of inorganic binders such as, for example, bentonite, which again leads to the supports being highly resistant to chemicals. Good resistance to chemicals is of particular advantage for use in the process according to the invention when working in corrosive, acid reaction media such as is the case, for example, during the purification of terephthalic acid.

In this case, the terephthalic acid is usually present in excess as compared with the contaminating aromatic aldehydes.

The catalytically active metal components are introduced into the calcined supports by known impregnation methods. Suitable impregnation methods are, for example, immersion impregnation or spray impregnation, taking into account the pore volume impregnation method. Spray impregnation is preferably used.

In the pore volume impregnation method, soluble precursors of the metal components are dissolved in an amount of water which corresponds to about 95% of the water absorption capacity of the support, wherein the metal content of the solution is adjusted to correspond to the desired metal content of the final catalysts. The solution is then sprayed onto the support revolving in a rotating drum, by means of a spray nozzle, preferably an ultrasonic spray nozzle.

Finally, the freshly prepared catalysts are dried for 15 minutes at 120° C. in a vortex dryer and then calcined, as described above.

The catalysts are activated in a stream of converting gas (95% $N_2$, 5% $H_2$) at 280° C. for a period of one hour. The precursors of the catalytically active metal components are reduced by this process.

According to the invention, the platinum group metals, Pt, Pd or Rh are used as catalytically active metal components. Suitable precursors for the impregnation method are water-soluble compounds of these noble metals such as, for example, halides, nitrates, amine complexes and nitrito or nitro complexes.

The use of chlorides or nitrates is not equivalent, but leads to catalytic systems with different activities and selectivities. When calcining the impregnated supports, the noble metal compounds are decomposed. Whereas nitrate can be removed from the catalyst without leaving any residues under reductive conditions, residues of chlorine remain on the catalyst support and confer acid properties thereto (J. A. R. von Veen; Z. f. Phys. Chem. 162 (1989) 215–229).

The profile of noble metal established over the cross section of the catalyst support depends on the type of noble metal salt, the pH of the impregnating solution and the time interval between impregnating and drying the support. Thoroughly impregnated catalysts are obtained, for example, by using $H_2PdCl_4$, $H_2PtCl_6$ or $RhCl_3$ and acidifying the impregnating solutions to a pH between 0 and 1. The result is a homogeneous catalyst. In contrast, shell-shaped profiles with shell thicknesses of up to 100 μm are obtained if the impregnating solution is adjusted to a pH of 5 with sodium hydroxide solution or if nitrate compounds of the noble metals are used instead of chloride compounds.

The impregnation profile can be measured optically in a simple way after activation by producing a cross-section. The reduced noble metal colors the otherwise white catalyst black at the impregnated sites.

The process according to the invention produces aromatic alcohols preferentially when the platinum group metal is palladium and when it is introduced into the support with a homogeneous distribution in the form of its chlorine compounds.

Very high activities and selectivities for the formation of aromatic alcohols are also obtained if palladium or platinum is introduced in the form of their nitrate compounds into the support with a shell-shaped distribution. These two process variants are particularly suitable for the removal, from p-hydroxymethyl benzoic acid, of the 4-carboxybenzaldehyde produced as a side product during synthesis by selective hydrogenation to give p-hydroxymethylbenzoic acid. In this case, the p-hydroxy-methylbenzoic acid itself, which is present in excess, must not be further hydrogenated.

Any suitable solvent inert to the reactants and under conditions used may be employed such as water, inert organic solvents including lower alcohols, preferably ethanol.

The second object of the invention is achieved by a process for preparing benzyl ethers from aromatic aldehydes of the formula:

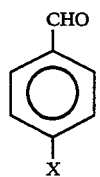

wherein X is methyl, carboxyl or a halogen.

The process is characterized in that the aromatic aldehydes are reacted in an alcoholic solution on a shaped support catalyst containing a platinum group metal on a support made of titanium oxide in the presence of hydrogen at hydrogen partial pressures of 5 to 50 bar and temperatures of 100° to 300° C. Preferably, a titanium oxide is used for the support which has been obtained from a precipitation process, is present in the anatase modification and has a pH of 5, preferably less than 3, as a 4% strength suspension in water. Palladium is preferably used as a platinum group metal for this process.

This process according to the invention supplies an elegant and simple way to obtain the product group of alkylaryl ethers. In comparison with the conventional, preparative chemical method of production by the Williams synthesis, it has the advantage that no salt wastes are produced at all. In this synthesis, the halogen anion on the alkylhalide compound is nucleophilically substituted by phenolation, wherein the alkylhalide compound must usually first be prepared from the corresponding alcohol. The catalytic process offers the additional advantage that it is a one-step process, in contrast with the two-step Williams process.

The invention is now explained in more detail by means of the examples.

The noble metal/titanium oxide catalysts ($NM/TiO_2$) C1 to C12 listed in Table 1 were prepared to perform the process according to the invention. A palladium/activated carbon catalyst (Pd/C) such as is used in the known hydrogenation processes acted as a comparison catalyst.

Catalysts C1 to C3, C7 and C10 and the comparison catalyst were prepared as shell-shaped catalysts with a shell thickness of less than 100 μm. For catalysts C1 to C3, $H_2PdCl_4$ was the palladium precursor. The shell formation was achieved by adjusting the pH of the impregnating solution to 5 by adding sodium hydroxide solution. The shell layers in catalysts C7 and C10 were produced by using palladium(II) nitrate, $Pd(NO_3)_2$ and platinum nitrate.

Catalysts C4 to C6, C8 to C9, C11 and C12 were prepared as thoroughly impregnated catalysts by using $H_2PdCl_4$, $H_2PtCl_6$ or $RhCl_3$ and acidifying the impregnating solution to a pH of 1 with HCl.

To characterize the metal dispersion, CO adsorption onto the metal crystallites was determined.

CO adsorption was lowest each time on the pure anatase catalysts (catalysts C1 and C4), at 0.1 and 0.19 ml CO/g of catalyst respectively, despite the large specific surface area of this material of at least 92 $m^2/g$. The best metal dispersion was in the catalysts with a phase ratio of anatase:rutile of 75:25. However, catalysts made from pure rutils with a specific surface area of only 18 $m^2/g$ also demonstrated a surprisingly high CO adsorption.

The process according to the invention was performed by way of example in an autoclave with a one liter capacity. The autoclave was fitted with a catalyst basket, an aeration stirrer and a sample withdrawal system. The following reaction conditions were used in the tests:

| charge/amount weighed out CHO-C₆H₄-X | solvent/ amount weighed (g) | added COOH-C₆H₄-COOH (g) | catalyst — amount weighed (g) | pH2* bar | T °C. | speed min⁻¹ |
|---|---|---|---|---|---|---|
| X = COOH/5 g | H₂O/495 | — | 2.0 | 10 | 150 | 1000 |
| X = COOH/5 g | H₂O/495 | 5 | 2.0 | 13 | 270 | 1000 |
| X = CH₃/5 g | C₂H₅OH/495 | — | 2.0 | 17 | 150 | 1000 |
| X = Cl/5 g | C₂H₅OH/495 | — | 2.0 | 17 | 150 | 1000 |

*Partial pressure of hydrogen at reaction temperature T.

The catalyst was placed in a basket and held in place by Raschig rings. The educt (starting material) and later the solvent were then introduced into the reaction chamber of the autoclave. The mix was heated to the reaction temperature with gentle stirring at 200 min⁻¹. After reaching the set temperature, the stirrer speed was increased to 1000 min⁻¹ and stirring continued for 15 min. Afterwards, a blank sample was withdrawn and then the hydrogen was introduced under pressure.

To follow the course of the reaction, further samples of 2.5 ml each were withdrawn after 0.17 hours (=ca. 10 min.), 1 hour, 2 hours and 4 hours respectively and dissolved in 3.5 molar NH₄OH solution (5.0 ml).

During hydrogenation of 4-carboxybenzaldehyde, the amount of unconverted educt or charge of initial starting material in the samples was determined by HPLC (High Pressure Liquid Chromatography). In this case, the samples were further diluted 500-fold using completely deionized water.

In the cases of hydrogenation of 4-chlorobenzaldehyde and p-toluylaldehyde, reaction of the educt (starting material) was followed using GC (Gas Chromatography).

EXAMPLE 1

Table 2 gives the activities and selectivities of a 0.5% Pd/C comparison catalyst (CC) based on a coconut shell activated support material and a 0.5% Pd/TiO₂ catalyst (C2) for the reaction of a 1% strength aqueous solution of 4-carboxybenzaldehyde (CBA) in the 1 l stirred autoclave at 150° C. and 10 bar hydrogen pressure.

The change in hydrogenation with time shows that the Pd/TiO₂ catalyst C2 is highly active and converts CBA at the same very high rate as the Pd/C comparison catalyst CC.

The Pd/C catalyst CC supplies p-hydroxymethylbenzoic (HMBA) acid with high selectivity, whereas with the Pd/TiO₂ catalyst C2 the result depends on the duration of the reaction, the alcohol component HMBA being produced at shorter reaction times and the product of hydrogenolysis, p-methylbenzoic acid (MBA), being produced at longer reaction times.

EXAMPLE 2

Table 3 gives the hydrogenation results for CBA when using Pd/TiO₂ catalysts with different anatase/rutile phase ratios in the TiO₂ support and with various Pd profiles.

The selectivity during hydrogenation of CBA is clearly influenced by using Pd/TiO₂ shell-shaped catalysts based on TiO₂ supports with different anatase/rutile phase ratios.

Thus, with the Pd/TiO₂ catalyst C1 based on a pure anatase support, HMBA is formed with a selectivity of more than 95% at a CBA conversion of 89%. On the other hand, Pd/TiO₂ catalyst C2, with a 25% rutile fraction in the support system, yields 55% of the hydrogenolysis product p-methyl-benzoic acid under the same reaction conditions.

With the Pd/TiO₂ catalyst C3 based on a pure rutile support, again up to 14.7% of the decarboxylation product benzoic acid is produced in addition to the main product HMBA.

In comparison with these results, these selectivity differences which depended on the TiO₂ modification were not observed when the Pd was uniformly distributed.

The Pd/TiO₂ catalyst systems C4 to C6 on anatase, anatase/rutile and rutile supports, on the other hand, were all characterized by very high rates of formation of HMBA, between 92.7 and 95.4%, and were superior to the Pd/C comparison catalyst CC.

EXAMPLE 3

Table 4 demonstrates the effect of the noble metal precursor used during preparation of Pd/TiO₂ catalyst systems on the selectivity.

The Pd/TiO₂ catalyst C2, impregnated with H₂PdCl₄, leads to a mixture of the hydrogenation product HMBA and the hydrogenolysis product MBA at almost quantitative conversion. When using Pd/TiO₂ catalyst C7 which was impregnated with Pd(NO₃)₂, on the other hand, the alcohol component HMBA was produced with very high selectivity. The rate of formation of HMBA was then about the same as with the Pd/C comparison catalyst CC.

EXAMPLE 4

Table 5 shows the effect of the Pd content of the Pd/TiO₂ catalyst system on selectivity and activity during hydrogenation of CBA.

The HMBA:MBA ratio can be specifically controlled by varying the Pd content in the Pd/TiO₂ catalyst system.

Benzyl alcohol is produced with high selectivity at high conversion using catalyst C5 with its small Pd coating of 0.5%. With increasing amounts of Pd, the MBA selectivity increases and at 2% Pd/TiO₂ the catalyst C9 has more than 37% selectivity for the hydrogenolysis product p-methyl-benzoic acid.

In parallel with this, hydrogenation activity increases with increasing Pd content, detectable from the increased conversion values after 1 hour's reaction time.

EXAMPLE 5

Table 6 shows the effect of the reaction parameters partial pressure of hydrogen and reaction temperature on the selectivity.

By increasing the partial pressure of hydrogen from 10 bar to 20 bar, the MBA selectivity rises to a value of more than 90% during the hydrogenation of CBA with the Pd/TiO$_2$ catalyst C9.

Increasing the reaction temperature by 100° to 250° C. produces more than 70% ring hydrogenation products such as 4-methylcyclohexanoic acid at quantitative conversion, when using Pd/TiO$_2$ catalyst C9.

EXAMPLE 6

Table 7 gives the test results for various Pt/TiO$_2$ and Rh/TiO$_2$ catalysts at 150° and 250° C.

The Pt/TiO$_2$ shell-shaped catalyst C10 prepared by the nitrate impregnation method gives p-hydroxymethylbenzoic acid with high selectivity.

The Pt/TiO$_2$ catalyst C11 with uniform distribution of Pt shows a much lower activity and also produces exclusively the alcohol component.

Raising the temperature by 100° to 250° C. shifts the selectivity in the direction of the hydrogenolysis product MBA and ring-hydrogenated products at now quantitative CBA conversion.

The Rh/TiO$_2$ catalyst C12 produces p-hydroxymethylbenzoic acid with a selectivity of >88% at 150° C. at a low degree of conversion.

At 250° C., with quantitative CBA conversion, 34.3% of benzoic acid is produced by decarboxylation and 37.7% of ring-hydrogenated products RH, in addition to 25% of the hydrogenolysis product MBA, after 4 hours reaction time.

EXAMPLE 7

Table 8 summarizes the results of CBA hydrogenation in the presence of terephthalic acid at 270° C. using the Pd/TiO$_2$ catalysts C1, C2, C3, C7 and the Pd/C comparison catalyst CC.

All the Pd/TiO$_2$ catalysts tested are mechanically and chemically stable in the presence of terephthalic acid under the drastic reaction conditions of 270° C.

Dissolution, mechanical separation or disintegration of the catalyst material did not occur.

This is attributed to the fact that the titanium oxide catalysts have a very high mechanical strength and the underlying TiO$_2$ support materials are acid resistant and have been shaped without the addition of inorganic binders which could dissolve in organic acids.

It is surprising that the NM/TiO$_2$ catalyst systems did not in general hydrogenate the terephthalic acid at the high temperatures of reaction, but highly selectively broke down the 4-carboxy-benzaldehyde.

The terephthalic acid concentration remained constant for all reactions over the whole course of hydrogenation.

The Pd/TiO$_2$ catalysts demonstrated the same trends in selectivity pattern for HMBA and MBA production as for CBA hydrogenation at 150° C. in the presence of terephtahalic acid, this depending on the anatase/rutile phase ratio in the underlying TiO$_2$ support.

The decarboxylation reaction to give benzoic acid which also occurs is attributed to the high reaction temperature. Using the Pd/C comparison catalyst CC, benzoic acid is formed as the main product with a selectivity of 55.6%.

The Pd/TiO$_2$ catalyst C1 based on pure anatase provides the highest HMBA selectivity, 71.4%, at relatively low CBA conversion. The hydrogenolysis product MBA is preferentially formed with the Pd/TiO$_2$ catalyst C2 based on the anatase/rutile mixed support.

The comparable Pd/TiO$_2$ catalyst C7 prepared using the nitrate impregnation method, produces a clear excess of HMBA as compared with MBA at approximately the same high rate of CBA conversion of more than 90%.

The hydrogenolysis reaction to give p-methylbenzoic acid is largely suppressed when using the rutile Pd/TiO$_2$ catalyst C3.

p-Hydroxymethylbenzoic acid is produced as the main hydrogenation product, with a selectivity of 61.5%, in addition to the decarboxylation product benzoic acid.

EXAMPLE 8

Table 9 gives the test results for the selective hydrogenation of p-methylbenzaldehyde.

The Pd, Pt and Rh/TiO$_2$ catalysts according to the invention show very obvious selectivity differences under the selected reaction conditions (150° C., ethanol as solvent, p=10 bar).

Thus, in Pd/TiO$_2$ catalyst systems, the selectivity for the various reaction products is determined solely by the variation in the anatase/rutile phase ratio in the TiO$_2$ support.

The Pd/TiO$_2$ catalyst Cl gives p-methylbenzyl ether with a selectivity of 99%. The preferred formation of the ether component is attributed to the acid fraction of the anatase support component, which catalyses etherification of the benzyl alcohol which is formed, by the solvent ethanol.

The use of Pd/TiO$_2$ catalyst C3 on a pure rutile support, on the other hand, leads to the formation of the corresponding benzyl alcohol with a selectivity of 64.5%. Etherification by the solvent is not observed due to the non-acidic properties of the rutile support.

With Pd/TiO$_2$ catalyst C2, the hydrogenolysis product p-xylene is formed as the main product, with a selectivity of more than 76%. The corresponding benzyl ether is formed as a side product.

In comparison with that, use of the less acid Pd/TiO$_2$ catalyst C7 suppresses etherification of the benzyl alcohol with an otherwise similar degree of p-xylene selectivity.

The Pt/TiO$_2$ catalyst C10 produces more than 84% benzyl alcohol or benzyl ether. In addition, a small conversion to the ring hydrogenation product 1,4-dimethylcyclohexane is observed.

The reaction catalysed by the Rh/TiO$_2$ catalyst produces the hydrogenolysis product p-xylene with a high selectivity, 76.1%, comparable to the Pd/TiO$_2$ catalyst C2.

EXAMPLE 9

Table 10 gives the test results for selective hydrogenation of 4-chlorobenzaldehyde on different NM/TiO$_2$ catalysts.

All the Pd/TiO$_2$ and Rh/TiO$_2$ catalysts tested demonstrate a high conversion activity under the selected reaction conditions (solvent ethanol, T=150° C., p=10 bar H$_2$).

By varying the TiO$_2$ phase ratio in the support material for the Pd/TiO$_2$ catalyst systems, the selectivity can be specifically controlled over a wide range.

Pd/TiO$_2$ catalyst C1 based on 100% anatase leads exclusively to ether components, which are formed by acid etherification of the corresponding 4-chlorobenzyl alcohol.

Pd/TiO$_2$ catalyst C2, on the other hand, largely causes the dehydrohalogenation of the hydrogenolysis product 4-chloro-toluene to give toluene.

Use of Pd/TiO$_2$ catalyst C3 based on pure rutile largely produces 4-chlorotoluene and, in comparison with catalyst C2, the dehydrohalogenation reaction is suppressed.

Pt/TiO$_2$ catalyst C10 leads to more than 64% of an approximately 1:1 mixture of 4-chlorobenzyl alcohol and 4-chlorobenzylethyl ether at low conversion rates. In addition, ring hydrogenation to give 1-chloro-4-methylcyclohexhane is also observed.

This ring hydrogenation reaction is the preferred reaction path with Rh/TiO$_2$ catalyst C12 and 1-chloro-4-methylcyclohexane is produced with a selectivity of just about 60%.

Further modifications and variations of the foregoing will be apparent to those skilled in the art and are intended to be encompassed by the claims appended hereto.

German priority application P 43 00 297.8 is relied on and incorporated herein by reference.

TABLE 1

Characterising the NM/TiO$_2$ catalysts
Extrudate diameter 3 mm; length 6 mm

| Cat. | Support | Modification Anatase | Rutile | Specific Surf. area (m$^2$/g) | NM | Amount % | NM outline | CO adsorption (ml CO/g cat) |
|---|---|---|---|---|---|---|---|---|
| CC | Activated carbon* | — | | 1170 | Pd | 0.5 | S | 0.19 |
| C1 | TiO$_2$ | 100 | 0 | 92 | Pd | 0.5 | S | 0.10 |
| C2 | TiO$_2$ | 75 | 25 | 50 | Pd | 0.5 | S | 0.32 |
| C3 | TiO$_2$ | 0 | 100 | 18 | Pd | 0.5 | S | 0.22 |
| C4 | TiO$_2$ | 100 | 0 | 92 | Pd | 0.5 | U | 0.19 |
| C5 | TiO$_2$ | 75 | 25 | 50 | Pd | 0.5 | U | 0.44 |
| C6 | TiO$_2$ | 0 | 100 | 18 | Pd | 0.5 | U | 0.34 |
| C7 | TiO$_2$ | 75 | 25 | 50 | Pd | 0.5 | S | 0.31 |
| C8 | TiO$_2$ | 75 | 25 | 50 | Pd | 1.0 | U | 0.50 |
| C9 | TiO$_2$ | 75 | 25 | 50 | Pd | 2.0 | U | 1.11 |
| C10 | TiO$_2$ | 75 | 25 | 50 | Pt | 1.0 | S | 0.38 |
| C11 | TiO$_2$ | 75 | 25 | 50 | Pt | 1.0 | U | 0.55 |
| C12 | TiO$_2$ | 75 | 25 | 50 | Rh | 1.0 | U | 1.72 |

*Particle size = 4 × 8 mesh
S = shell distribution; U = uniform distribution

TABLE 2

Comparison of catalyst stability of a Pd/C comparison catalyst and a Pd/TiO$_2$ catalyst

| Cat. | Support | Modification Anatase | Rutile | NM | Amount (%) | Prof. | Reactn. time (h) | Conversion (%) CBA-CHO-COOH | Selectivity (%) HMBA-CH$_2$OH-COOH | MBA-CH$_3$-COOH | BA-COOH |
|---|---|---|---|---|---|---|---|---|---|---|---|
| CC | Activ. carbon | — | | Pd | 0.5 | S | 0.17 | 54.0 | 99.3 | 0.7 | 0.0 |
| | | | | | | | 1.0 | 98.8 | 94.1 | 5.8 | 0.0 |
| | | | | | | | 2.0 | 99.8 | 92.0 | 7.9 | 0.0 |
| | | | | | | | 4.0 | 99.9 | 91.4 | 8.6 | 0.0 |
| C2 | TiO$_2$ | 75 | 25 | Pd | 0.5 | S | 0.17 | 51.4 | 98.9 | 1.1 | 0.0 |
| | | | | | | | 1.0 | 99.8 | 72.3 | 27.6 | 0.1 |
| | | | | | | | 2.0 | 99.9 | 55.0 | 44.6 | 0.3 |
| | | | | | | | 4.0 | 99.9 | 44.7 | 55.1 | 0.2 |

CBA: 4-carboxybenzaldehyde
HMBA: p-hydroxymethylbenzoic acid
MBA: p-methylbenzoic acid
BA: benzoic acid
Prof. profile

TABLE 3

Effect of TiO$_2$ modification and Pd profile on selectivity

| Cat. | Support | Modification Anatase | Rutile | NM | Amount (%) | Prof. | Reactn. time (h) | Conversion % CBA | Selectivity HMBA | MBA | BA |
|---|---|---|---|---|---|---|---|---|---|---|---|
| C1 | TiO$_2$ | 100 | 0 | Pd | 0.5 | S | 4 | 89.2 | 95.6 | 3.9 | 0.2 |
| | | | | | | | 1 | 56.2 | 97.4 | 2.0 | 0.3 |
| C2 | TiO$_2$ | 75 | 25 | Pd | 0.5 | S | 4 | 99.9 | 44.7 | 55.1 | 0.2 |
| | | | | | | | 1 | 99.8 | 72.3 | 27.6 | 0.1 |
| C3 | TiO$_2$ | 0 | 100 | Pd | 0.5 | S | 4 | 99.7 | 85.1 | 0.1 | 14.7 |
| | | | | | | | 1 | 89.7 | 98.7 | 0.1 | 1.2 |
| C4 | TiO$_2$ | 100 | 0 | Pd | 0.5 | U | 4 | 96.6 | 96.0 | 3.6 | 0.3 |
| | | | | | | | 1 | 71.2 | 97.7 | 2.1 | 0.0 |
| C5 | TiO$_2$ | 75 | 25 | Pd | 0.5 | U | 4 | 99.4 | 93.8 | 4.8 | 1.4 |
| | | | | | | | 1 | 90.9 | 98.2 | 0.4 | 1.5 |
| C6 | TiO$_2$ | 0 | 100 | Pd | 0.5 | U | 4 | 97.3 | 98.0 | 1.4 | 0.4 |

TABLE 3-continued

Effect of TiO₂ modification and Pd profile on selectivity

| Cat. | Support | Modification Anatase | Rutile | NM | Amount (%) | Prof. | Reactn. time (h) | Conversion % CBA | Selectivity HMBA | MBA | BA |
|---|---|---|---|---|---|---|---|---|---|---|---|
| | | | | | | | 1 | 68.0 | 99.1 | 0.0 | 0.7 |

TABLE 4

Effect of noble metal precursor for the catalyst on the selectivity

| Cat | Support | Modification Anatase | Rutile | NM | Amt. | Prof. | Prep. | Reactn. time (h) | Conv. % CBA | Selectivity HMBA | MBA | BA |
|---|---|---|---|---|---|---|---|---|---|---|---|---|
| C2 | TiO₂ | 75 | 25 | Pd | 0.5 | S | H₂PdCl₄ | 4 | 99.9 | 44.7 | 55.1 | 0.2 |
| | | | | | | | | 1 | 99.8 | 72.3 | 27.6 | 0.1 |
| C7 | TiO₂ | 75 | 25 | Pd | 0.5 | S | Pd(NO₃)₂ | 4 | 99.7 | 92.3 | 7.4 | 0.2 |
| | | | | | | | | 1 | 82.2 | 99.1 | 0.3 | 0.4 |

Prep.: Noble metal precursor for preparing the catalysts.

TABLE 5

Effect of the amount of Pd

| Cat. | Support | Modification Anatase | Rutile | NM | Amount (%) | Reactn. time (h) | Convers. (%) | Selectivity (%) HMBA | MBA | BA |
|---|---|---|---|---|---|---|---|---|---|---|
| C5 | TiO₂ | 75 | 25 | Pd | 0.5 | 4 | 99.4 | 93.8 | 4.8 | 1.4 |
| | | | | | | 1 | 90.9 | 98.2 | 0.4 | 1.5 |
| C8 | TiO₂ | 75 | 25 | Pd | 1.0 | 4 | 99.6 | 71.5 | 28.4 | 0.1 |
| | | | | | | 1 | 94.2 | 95.5 | 4.3 | 0.5 |
| C9 | TiO₂ | 75 | 25 | Pd | 2.0 | 4 | 99.7 | 62.3 | 37.4 | 0.1 |
| | | | | | | 1 | 97.1 | 94.7 | 5.0 | 0.1 |

TABLE 6

Effect of reaction temperature and hydrogen partial pressure on selectivity

| Cat. | Support | Modification Anatase | Rutile | NM | Amount (%) | Prof. | React. condit. t [h] | T [°C] | pH₂ [bar] | Conv. % CBA | Selectivity (%) HMBA | NMA | BA | RH* |
|---|---|---|---|---|---|---|---|---|---|---|---|---|---|---|
| C9 | TiO₂ | 75 | 25 | Pd | 2.0 | U | 4 | 150 | 10 | 99.7 | 62.3 | 37.4 | 0.1 | 0.0 |
| | | | | | | | 1 | | | 97.1 | 94.7 | 5.0 | 0.1 | 0.0 |
| C9 | TiO₂ | 75 | 25 | Pd | 2.0 | U | 4 | 150 | 20 | 99.8 | 0.9 | 90.5 | 0.0 | 8.6 |
| | | | | | | | 1 | | | 97.5 | 56.3 | 43.7 | 0.0 | 0.0 |
| C9 | TiO₂ | 75 | 25 | Pd | 2.0 | U | 4 | 250 | 20 | 100.0 | 0.5 | 28.2 | 0.4 | 70.9 |
| | | | | | | | 1 | | | 99.3 | 14.3 | 66.6 | 3.7 | 15.4 |

RH: Ring-hydrogenated reaction products
pH₂ Partial pressure of hydrogen at the reaction temperature
React. Condit. Reaction conditions

TABLE 7

Effect of noble metal and reaction temperature on selectivity

| Cat. | Support | Modification Anatase | Rutile | NM | Amount (%) | Prof. | Reac. cond. t [h] | T [°C] | Conv (%) CBA | Selectivity (%) HMBA | MBA | BA | RH |
|---|---|---|---|---|---|---|---|---|---|---|---|---|---|
| C10 | TiO₂ | 75 | 25 | Pt | 1.0 | S | 4 | 150 | 99.3 | 92.6 | 7.1 | 0.1 | 0.0 |
| | | | | | | | 1 | | 93.8 | 99.6 | 0.0 | 0.2 | 0.0 |
| C11 | TiO₂ | 75 | 25 | Pt | 1.0 | U | 4 | 150 | 36.1 | 100.0 | 0.0 | 0.0 | 0.0 |
| | | | | | | | 1 | | 10.8 | 100.0 | 0.0 | 0.0 | 0.0 |
| C11 | TiO₂ | 75 | 25 | Pt | 1.0 | U | 4 | 250 | 99.9 | 13.0 | 47.5 | 8.6 | 30.9 |
| | | | | | | | 1 | | 87.6 | 62.8 | 16.0 | 12.7 | 8.5 |
| C12 | TiO₂ | 75 | 25 | Rh | 1.0 | U | 4 | 150 | 40.8 | 88.1 | 5.5 | 6.4 | 0.0 |
| | | | | | | | 1 | | 13.8 | 100.0 | 0.0 | 0.0 | 0.0 |
| C12 | TiO₂ | 75 | 25 | Rh | 1.0 | U | 4 | 250 | 99.9 | 2.7 | 25.3 | 34.3 | 37.7 |
| | | | | | | | 1 | | 57.0 | 28.4 | 6.3 | 49.3 | 16.0 |

TABLE 8

Selectivity for CBA hydrogenation in the presence of terephthalic acid at 270° C.

| Cat. | Support | Modification Anatase | Rutile | NM | Amount (%) | Prof. | React. time (h) | Convers (%) CBA | Selectivity HMBA | MBA | BA |
|---|---|---|---|---|---|---|---|---|---|---|---|
| CC | Act. Carbon | — | — | Pd | 0.5 | S | 4 | 99.7 | 20.4 | 23.9 | 55.6 |
| C1 | TiO₂ | 100 | 0 | Pd | 0.5 | S | 4 | 37.6 | 71.4 | 22.9 | 5.7 |
| C2 | TiO₂ | 75 | 25 | Pd | 0.5 | S | 4 | 90.5 | 32.3 | 39.6 | 28.1 |
| C3 | TiO₂ | 0 | 100 | Pd | 0.5 | S | 4 | 83.4 | 61.5 | 5.5 | 33.0 |

TABLE 8-continued

Selectivity for CBA hydrogenation in the presence of terephthalic acid at 270° C.

| | | Modification | | | Amount | | React. | Convers (%) | Selectivity | | |
|---|---|---|---|---|---|---|---|---|---|---|---|
| Cat. | Support | Anatase | Rutile | NM | (%) | Prof. | time (h) | CBA | HMBA | MBA | BA |
| C7 | TiO$_2$ | 75 | 25 | Pd | 0.5 | S | 4 | 90.1 | 48.3 | 16.8 | 34.3 |

TABLE 9

Selective hydrogenation of p-methylbenzaldehyde on NM/TiO$_2$ catalysts

| | | Modification | | | | | | Conv. (%) | Selectivity (%) | | | | |
|---|---|---|---|---|---|---|---|---|---|---|---|---|---|
| | | | | | | | | CHO–C$_6$H$_4$–CH$_3$ | CH$_2$OR–C$_6$H$_4$–CH$_3$ | | CH$_3$–C$_6$H$_4$–CH$_3$ | CH$_3$–C$_6$H$_{10}$–CH$_3$ | CH$_3$–C$_6$H$_5$ |
| Cat. | Support | Anat. | Rut. | NM | Amt. (%) | Prof. | Reac. time (h) | CH$_3$ | R = H | R = C$_2$H$_5$ | CH$_3$ | CH$_3$ | Other |
| C1 | TiO$_2$ | 100 | 0 | Pd | 0.5 | S | 4 | 74.1 | 0.0 | 99.0 | 0.0 | 1.0 | |
| C2 | TiO$_2$ | 75 | 25 | Pd | 0.5 | S | 4 | 78.9 | 0.0 | 21.9 | 76.8 | 1.3 | |
| C3 | TiO$_2$ | 0 | 100 | Pd | 0.5 | S | 4 | 62.9 | 64.5 | 2.4 | 33.2 | 0.0 | |
| C7 | TiO$_2$ | 75 | 25 | Pd | 0.5 | S | 4 | 95.7 | 16.2 | 7.7 | 74.2 | 2.0 | |
| C10 | TiO$_2$ | 75 | 25 | Pt | 1.0 | S | 4 | 46.5 | 35.2 | 48.9 | 2.3 | 10.8 | 2.8 |
| C12 | TiO$_2$ | 75 | 25 | Rh | 1.0 | U | 4 | 78.8 | 0.0 | 15.5 | 76.1 | 6.3 | 2.1 |

TABLE 10

Selective hydrogenation of 4-chlorobenzaldehyde on NM/TiO$_2$ catalysts

| | | Modification | | | | | | Conver. (%) | Selectivity (%) | | | | |
|---|---|---|---|---|---|---|---|---|---|---|---|---|---|
| | | | | | | | | CHO–C$_6$H$_4$–Cl | CH$_2$OR–C$_6$H$_4$–Cl | | CH$_3$–C$_6$H$_4$–Cl | CH$_3$–C$_6$H$_{10}$–Cl | CH$_3$–C$_6$H$_5$ |
| Cat. | Support | Anat. | Rut. | NM | Amt. (%) | Prof. | React. time (h) | Cl | R = H | R = C$_2$H$_5$ | Cl | Cl | |
| C1 | TiO$_2$ | 100 | 0 | Pd | 0.5 | S | 4 | 84.7 | 0.0 | 100.0 | 0.0 | 0.0 | 0.0 |
| C2 | TiO$_2$ | 75 | 25 | Pd | 0.5 | S | 4 | 78.2 | 0.0 | 15.0 | 18.7 | 3.1 | 62.2 |
| C3 | TiO$_2$ | 0 | 100 | Pd | 0.5 | S | 4 | 91.2 | 0.0 | 10.2 | 30.1 | 4.8 | 54.9 |
| | | | | | | | 1 | 33.7 | 0.0 | 16.5 | 44.6 | 0.0 | 38.9 |
| C10 | TiO$_2$ | 75 | 25 | Pt | 1.0 | S | 4 | 24.2 | 27.9 | 36.3 | 0.0 | 35.0 | 0.0 |
| C12 | TiO$_2$ | 75 | 25 | Rh | 1.0 | U | 4 | 88.1 | 0.0 | 15.5 | 4.2 | 58.5 | 21.7 |

We claim:

1. A process for the selective catalytic hydrogenation of carbonyl groups in an aromatic aldehyde of the formula:

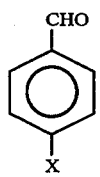

in which X is carboxyl, methyl or halogen, to yield the corresponding alcohol or methyl compound, comprising reacting said aromatic aldehyde with hydrogen at hydrogen partial pressures of 5 to 50 bar and temperatures of 100° to 300° C. to hydrogenate said aromatic aldehyde in the presence of a solvent, optionally in the presence of an organic acid, on a shaped support catalyst containing a platinum group metal on a support made from titanium oxide.

2. A process according to claim 1, wherein the titanium oxide is a titanium oxide prepared by a precipitation process or by flame hydrolysis and is present in the anatase or rutile form or as mixtures or mixed phases thereof.

3. A process according to claim 1 wherein the shaped support catalyst contains no inorganic binder.

4. A process according to claim 1 wherein the support catalyst has external dimensions of 1 to 10 mm and a breaking strength greater than 40N.

5. A process according to claim 1 wherein the platinum group metal is platinum, palladium or rhodium and is present in an amount of 0.01 to 3.0% by weight, with reference to the weight of the support.

6. A process according to claim 1 wherein hydrogenation is performed in the presence of terephthalic acid which may be present in excess with respect to the aromatic aldehyde.

7. A process according to claim 1 wherein the support catalyst is obtainable by impregnating the support made from titanium oxide with a water-soluble chlorine or nitrate compound of the platinum group metal, followed by drying and calcining and activating in a stream of gas which contains hydrogen.

8. A process according to claim 7, wherein the platinum group metal is palladium and is introduced onto the support with homogeneous distribution in the form of its chlorine compounds.

9. A process according to claim 7, wherein the platinum group metal is palladium and is introduced onto the support with a shell-shaped distribution in the form of its nitrate compounds.

10. A process according to claim 7, wherein the platinum group metal is platinum and is introduced onto the support with a shell-shaped distribution in the form of its nitrate compounds.

11. A process according to claim 8 wherein hydrogenation is performed in the presence of p-hydroxymethylbenzoic acid and the organic acid may be present in excess with respect to the aromatic aldehyde.

12. A process according to claim 9 wherein hydrogenation is performed in the presence of p-hydroxymethylbenzoic acid and the organic acid may be present in excess with respect to the aromatic aldehyde.

* * * * *